United States Patent
Chien

(10) Patent No.: US 10,085,661 B2
(45) Date of Patent: Oct. 2, 2018

(54) SYSTEM AND METHOD FOR BIVENTRICULAR PACEMAKER PULSE DETECTION IN SURFACE ECG

(71) Applicant: KONINKLIJKE PHILIPS N.V., Eindhoven (NL)

(72) Inventor: Cheng-hao Chien, Thousand Oaks, CA (US)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 14/784,594

(22) PCT Filed: Apr. 16, 2014

(86) PCT No.: PCT/IB2014/060750
§ 371 (c)(1),
(2) Date: Oct. 15, 2015

(87) PCT Pub. No.: WO2014/170832
PCT Pub. Date: Oct. 23, 2014

(65) Prior Publication Data
US 2016/0058317 A1 Mar. 3, 2016

Related U.S. Application Data

(60) Provisional application No. 61/812,313, filed on Apr. 16, 2013.

(51) Int. Cl.
*A61B 5/04* (2006.01)
*A61B 5/00* (2006.01)
(Continued)

(52) U.S. Cl.
CPC ........ *A61B 5/04011* (2013.01); *A61B 5/0402* (2013.01); *A61B 5/04017* (2013.01);
(Continued)

(58) Field of Classification Search
CPC .... A61N 1/3622; A61N 1/368; A61N 1/3682; A61N 1/3684; A61N 1/36868;
(Continued)

(56) References Cited

U.S. PATENT DOCUMENTS 6,304,772 B1  10/2001  Taha et al.
2003/0083586 A1  5/2003  Ferek-Petric
(Continued)

FOREIGN PATENT DOCUMENTS

CN  101011242 A  8/2007

OTHER PUBLICATIONS

S. C. Chien, P. C. Chang, H. T. Wo, C. C. Wang, M. S. Wen and E. D. Helfenbein, "Vector-based pacemaker pulse detection algorithm for the surface ECG," Computing in Cardiology 2014, Cambridge, MA, 2014, pp. 741-744.*
(Continued)

*Primary Examiner* — Eugene T Wu

(57) ABSTRACT

A system for locating the existence of a biventricular pace pulse for ECG, which includes a non-biventricular pulse detector for finding the onsets of ventricular pulses, a lead-wise biventricular pulse detector for checking whether there are two separated ventricular pulses in one heartbeat, and a vector-based biventricular pulse detector for determining the existence of the biventricular pace pulse if the lead-wise biventricular pulse detector does not find that there are two separated ventricular pulses in one heartbeat.

13 Claims, 10 Drawing Sheets

(51) Int. Cl.
*A61B 5/0452* (2006.01)
*A61B 5/0402* (2006.01)

(52) U.S. Cl.
CPC .......... *A61B 5/0452* (2013.01); *A61B 5/7217* (2013.01); *A61B 5/7264* (2013.01)

(58) Field of Classification Search
CPC ...... A61N 1/3688; A61N 1/37; A61N 1/3706; A61N 1/371; A61B 5/0245; A61B 5/04011; A61B 5/04012; A61B 5/0402; A61B 5/0432; A61B 5/04325; A61B 5/0452; A61B 5/0456; A61B 5/7221; A61B 5/7235; A61B 5/7264; A61B 5/7271; A61B 5/7282; A61B 5/7285; A61B 5/7289
See application file for complete search history.

(56) References Cited

U.S. PATENT DOCUMENTS

2004/0102812 A1 5/2004 Yonce et al.
2016/0058317 A1 3/2016 Chen
2016/0143891 A1 5/2016 Shalwitz et al.

OTHER PUBLICATIONS

"Finite difference". Wikipedia. <https://en.wikipedia.org/wiki/Finite_difference>. Accessed Jun. 19, 2017.*
Eric D. Helfenbein et al; "A Software-Based Pacemaker Pulse Detection and Paced Rhythm Classification Algorithm", Journal of Electrocardiology, vol. 35, 2002, pp. 95-103.
Anthony D. Ricke et al; "Improved Pacemaker Pulse Detection: Clinical Evaluation of a New High-Bandwidth Electrocardiographic System", Journal of Electrocardiology, vol. 44, 2011, pp. 265-274.
Jonathon Koenig et al; "Observations of Pacemaker Pulses in High-Bandwidth Electrocardiograms and Dower-Estimated Vectorcardiograms", Journal of Electrocardiology, vol. 44, No. 2, Apr. 30, 2011, pp. 275-281, XP028152274.
J. A. A. Fairweather et al; "Computer Analysis of Implanted Cardiac Pacemaker Rhythm", Computers in Cardiology, Sep. 30, 2007, IEEE, Piscataway, NJ, USA, pp. 193-196, XP031404680.
Lall, C. et al., "Perfomance challenges in ECG pacemaker pulse detection systems", Computing in Cardiology (CinC), 2012, IEEE, pp. 765-768.

* cited by examiner

VCG features

502 — VCG: $\bar{V} = (\bar{V}_0, \bar{V}_1, \ldots \bar{V}_k, \ldots), \bar{V}_k = \begin{pmatrix} x_k \\ y_k \\ z_k \end{pmatrix}$ 601 — Spatial distance: $d_k = |\bar{V}_k| = \sqrt{x_k^2 + y_k^2 + z_k^2}$ 703 — Spatial velocity: $v_k = |\bar{V}_k - \bar{V}_{k-1}| = \sqrt{(x_k - x_{k-1})^2 + (y_k - y_{k-1})^2 + (z_k - z_{k-1})^2}$ 603 — Spatial angle: $a_k = \dfrac{\bar{V}_j^T \bar{V}_k}{|\bar{V}_j| |\bar{V}_k|}$

SYSTEM AND METHOD FOR BIVENTRICULAR PACEMAKER PULSE DETECTION IN SURFACE ECG

This application is a national stage application under 35 U.S.C. § 371 of International Application No. PCT/IB2014/060750 filed on Apr. 16, 2014 and published in the English language on Oct. 23, 2014 as International Publication No. WO2014/170832 A1, which claims priority to United States Application Serial No. 61/812,313, filed on Apr. 16. 2013, the entire disclosures of which are incorporated herein by reference.

The present disclosure relates to, e.g., medical systems, methods and devices, and more particularly to novel and inventive system and method for biventricular pacemaker pulse detection in surface ECG.

An increasing number of heart failure patients are receiving Cardiac Resynchronization Therapy (CRT), which uses pacing of both left and right ventricles to maximize cardiac output. Non-synchronous biventricular (biV) pacemaker pulses (pp) in the surface electrocardiograph (ECG) waveform create challenges for computerized diagnostic ECG analysis algorithms. For example, a pulse detection algorithm not designed for recognizing non-synchronous biV pulses can fail due to the closely-separated pair of ventricular pulses, and the undetected and unresolved pulses can consequently have a detrimental impact on the automated diagnostic ECG algorithm's rhythm or morphology interpretations. On the other hand, being able to recognize the existence of biventricular pacemaker pulses in the surface ECG is important for accurate diagnosis.

Non-synchronous biventricular (biV) pacemaker pulses are closely spaced in time, and provide challenges to automated diagnostic ECG algorithms which need to detect both ventricular chamber pulses. A special pacemaker pulse detection algorithm is needed to recognize biV pulses, as undetected and unresolved pulses may consequently have a detrimental impact on the diagnostic ECG algorithm's rhythm or morphology interpretations.

One approach to detect biV pulses would be to replace the data acquisition hardware with a front-end having a higher sample rate (e.g., in the multi-kilo-hertz range) to better preserve the morphology of both pulses. However, such an approach is generally not suitable for existing cardiographs nor for retrospective analysis on a central server of collected data which has been low-pass filtered at 150 Hz. and stored with a sample rate of 500 sps. Indeed, a typical ECG processing system applies a 150 Hz low-pass filter on the ECG signal and stores it at a sample rate of 500 sps, generally making retrospective biV pp detection much more difficult.

Disclosed and described herein is a system and method for biV pulse detection that does not require hardware modification. Exemplary embodiments of the present invention can analyze the pulses identified by the existing non-biV pulse detection system and method and combine that information with the spatial vector of the ECG signal to detect closely-spaced biV pulses.

In accordance with exemplary embodiments of the present disclosure, a system and method are provided which are able to process the type of signal using a 3-D vector, so that biV pp detection can be done in post-processing or on a central server, for example. Exemplary embodiments of the present invention can be incorporated with certain existing non-biV pacemaker pulse detection systems and methods with relatively minimal modification.

For example, in accordance with an exemplary embodiment of the present disclosure, a vector-based biventricular pace pulse detector is provided which includes a processor configured to calculate VCG distance features, find a first ventricular pulse, calculate VCG angle features, and determine the existence of the biventricular pace pulse based on at least one of the VCG distance features and the VCG angle features. The detector can also include an input configured to receive ECG data, and the processor can be further configured to transform the ECG data to a 3-dimensional VCG. The detector can further include a pulse classifier configured to determine the existence of the biventricular pace pulse based on the VCG distance features and/or the VCG angle features. The pulse classifier can be configured to reject an impulse response of a low-pass filter and/or to reject a recharging wave to determine the existence of the biventricular pace pulse.

In accordance with another exemplary embodiment of the present disclosure, provided is a system for locating the existence of a biventricular pace pulse for ECG. The exemplary system includes a non- biventricular pulse detector configured to find the onsets of one or more ventricular pulses, a lead-wise biventricular pulse detector for determining whether there are two separated ventricular pulses in one heartbeat, and a vector-based biventricular pulse detector configured to determine the existence of the biventricular pace pulse if the lead-wise biventricular pulse detector does not determine that there are two separated ventricular pulses in one heartbeat. The vector-based biventricular pulse detector can be further configured to calculate VCG distance features, find a first ventricular pulse, calculate VCG angle features, and determine the existence of the biventricular pace pulse based on the VCG distance features and/or the VCG angle features. The exemplary system can further include a pulse classifier configured to determine the existence of the biventricular pace pulse based on the VCG distance features and/or the VCG angle features. The pulse classifier can be configured to reject an impulse response of a low-pass filter and/or a recharging wave, to determine the existence of the biventricular pulse.

According to yet another exemplary embodiment of the present disclosure, a method for locating the existence of a biventricular pace pulse for ECG is provided. The exemplary method includes transforming ECG data to a 3-dimensional VCG, calculating VCG distance features, locating a first ventricular pulse, calculating VCG angle features, and determining the existence of the biventricular pace pulse based on the VCG distance features and/or the VCG angle features. The exemplary method can further include obtaining the ECG data. The ECG data can include two adjacent ventricular pulses per heartbeat or two partially overlapping ventricular pulses per heartbeat, for example.

IN THE DRAWINGS

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof

DETAILED DESCRIPTION

As noted above, an increasing number of chronic heart failure patients receive CRT. CRT paces both left and right ventricles with an adjustable interval to maximize cardiac output. Due to the evolving market of CRT, recognizing biventricular pp on the surface ECG can become a critical issue for an automatic ECG analysis system and method. Existing known methods tend to require high sample rate hardware. In contrast, the present disclosure describes, e.g., a novel system and method to detect biventricular pp on the typical sample rate and low-pass filtered ECG signal.

As indicated above, biventricular (biV) pacemaker uses pacing both left and right ventricles to maximize the cardiac output. The two pacemaker pulses (pp) can be synchronous or non-synchronous. It is generally possible to recognize non-synchronous biV pulses from surface ECG with a data acquisition device with high sampling rate (>5000 sps). The usual sample rate of ECG is 500 sps for efficient storage of data, and the signal is usually 150 Hz low-pass filtered to remove noise. The regular sampling rate and the built-in low-pass filter widens pace pulses, so the closely-separated pair of ventricular pulses can be indistinguishable and look like a single wide pulse or a single pulse followed by ripples on a single lead.

Figure 1:
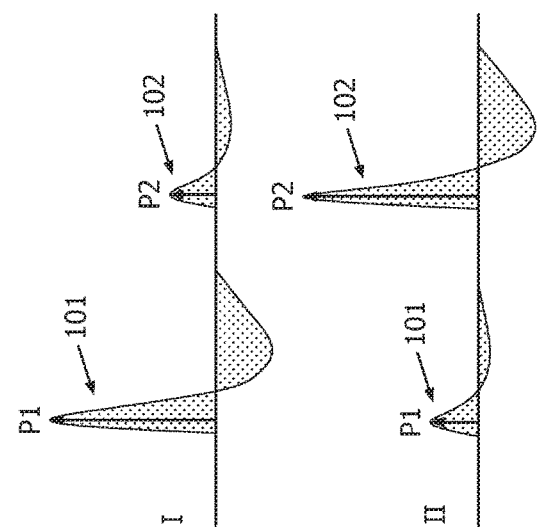
FIG. 1 is an illustration showing an example of separable ventricular pulses, in accordance with the present disclosure.
Figure 1:
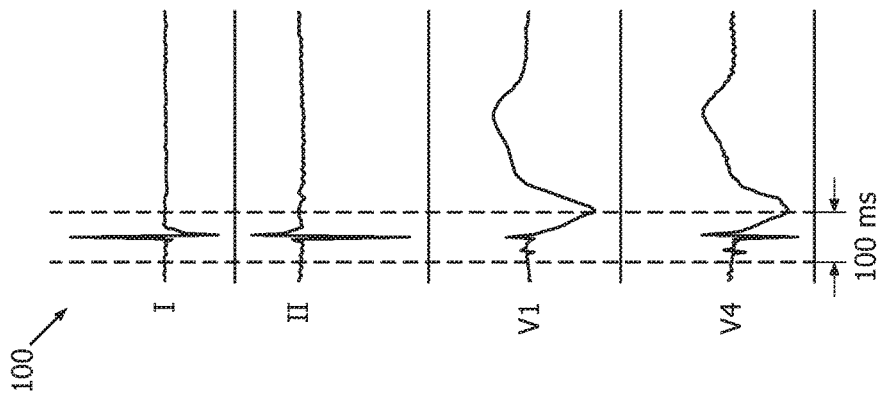
Figure 2:
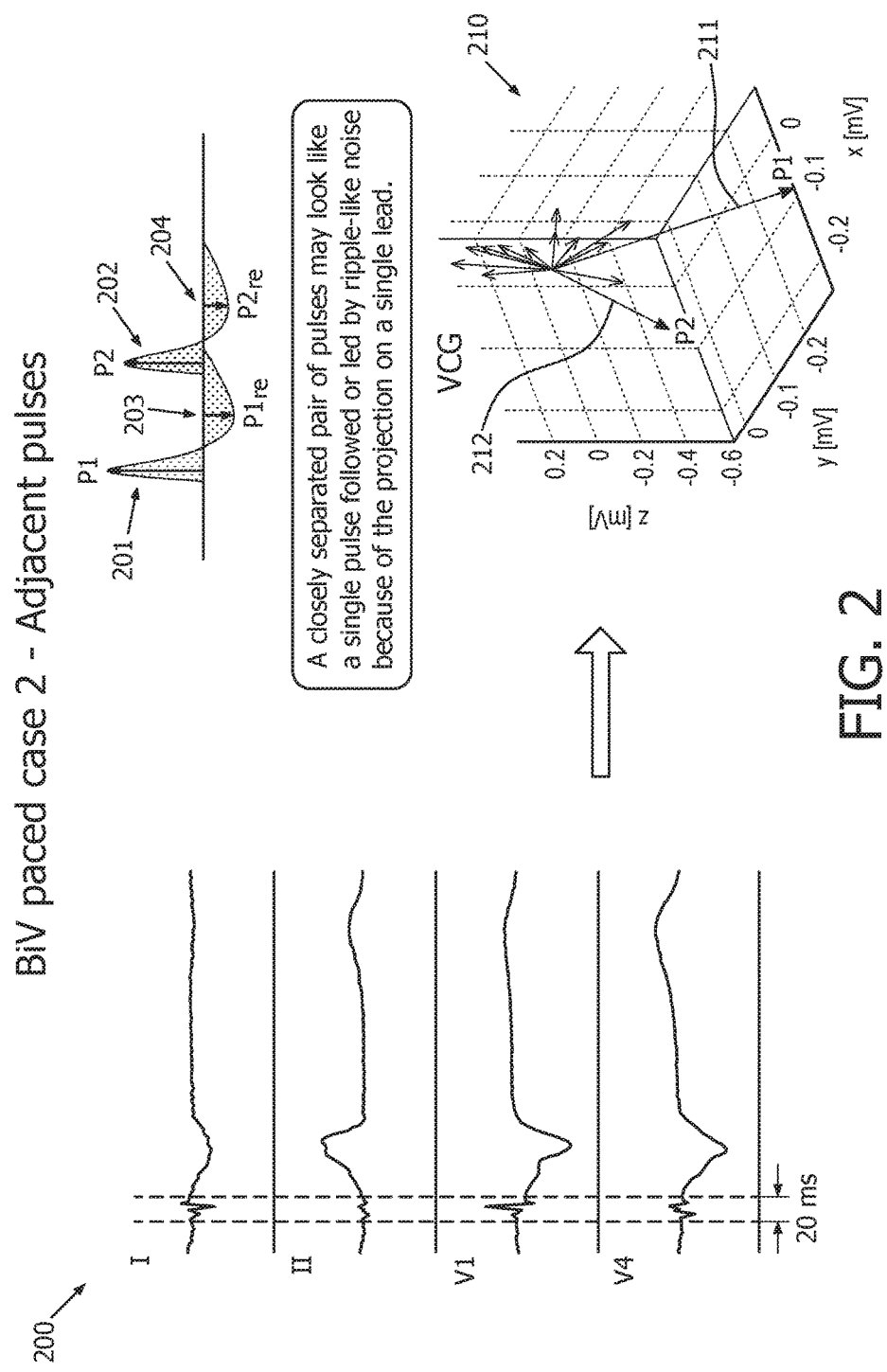
FIG. 2 is an illustration showing an example of adjacent ventricular pulses, in accordance with the present disclosure.
Figure 3:
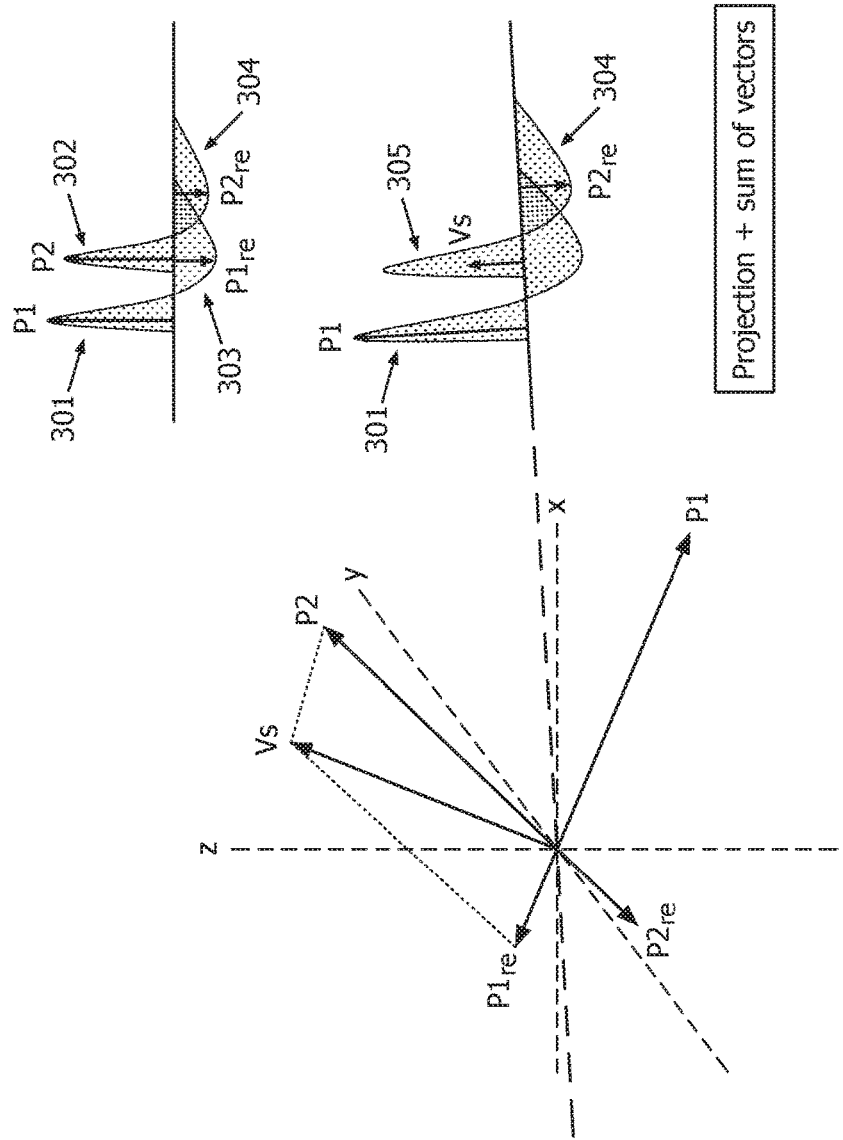
FIG. 3 is an illustration showing an example of partially overlapped, ventricular pulses in accordance with the present disclosure.

For example, FIGS. 1-3 illustrate three possible scenarios: separable, adjacent and partially overlapped ventricular pulses.

As illustrated in FIG. 1, for example, separable pulses are typically distant enough, so a non-biV pulse detection algorithm may still be able to identify the existence of two distinct ventricular pulses by looking across leads. Graph 100 shows the single beat ECG waveforms of leads I, II, V1 and V4 in a sampling window of 100 msec, in which there are clearly two pulses. Pulse P1 101 and Pulse P1 102 are each sufficiently distant from one another so that there is no overlap between the two pulses, including their respective recharge pulses. The two pulses are separable, because the V-V interval (corresponding to the P1-P2 interval), is enough to see the two distinct pulses across the leads.

As illustrated in FIG. 2, for example, adjacent ventricular pulses generally will not look like two pulses due to the projection of vectors, so a non-biV pulse detection algorithm will typically not be able to detect the existence of two ventricular pulses. Graph 200 shows the single beat ECG waveforms of leads I, II, V1 and V4 in a sampling window of 20 msec, in which two pulses cannot clearly be seen. The two pulses P1 201 and P2 202, along with their respective recharge pulses P1re 203 and P2re 204, may look like a single pulse followed or led by ripple-like noise, due to the angle between the two pulse vectors and the projection angle to the measurement lead. Three dimensional graph 210 provides a graphical illustration of vectors 211 and 212 corresponding to Pulses P1 201 and P2 202, respectively. In this scenario, for example, if a pace pulse detection algorithm cannot recognize the existence of the second ventricular pulse, the pulse will not be removed, and then the automated diagnostic analysis based on this waveform will not be accurate.

As illustrated in FIG. 3, for example, partially overlapped pulses P1 301 and P2 302 have the recharging wave of the first pulse P1re 303 overlapping with the discharging wave of the second ventricular pulse P2 302. As a result, P1re 303 and P2 302 will typically show as a single combined pulse or vector Vs 305. As a result, in this scenario as well, for example, if a pace pulse detection algorithm cannot recognize the existence of the second ventricular pulse, the pulse will not be removed, and then the automated diagnostic analysis based on this waveform will not be accurate.

Figure 4:
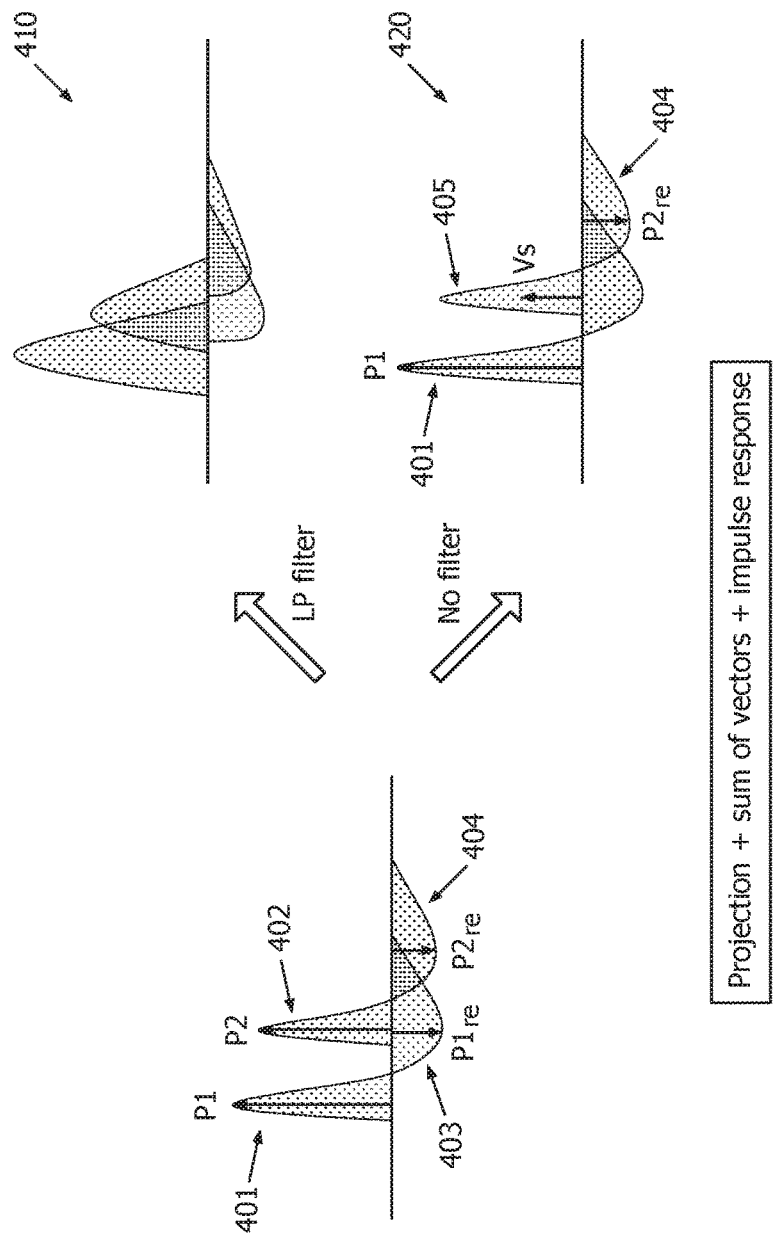
FIG. 4 is an illustration showing an example of a low-Pass filter making pulses wider and more difficult to be separated, in accordance with the present disclosure.

As shown in FIG. 4, a low-Pass filter will typically make a pace pulse wider, so, e.g., two adjacent pulses P1 401 and P2 402 could become unseparated and overlapped on the surface ECG, or the two overlapped pulses could result in more complicated sum of vectors, as shown in graphic 410, for example. Indeed, it can be particularly difficult to separate two pulses subject to a low-Pass filter, as much depends on the details of the specific filter. As shown in graphic 420, for example, similarly to the scenario illustrated in FIG. 3, when no filter is used, the result which is seen is pulse P1 401 followed by a single combined pulse or vector Vs 405, followed by pulse P2 402.

Accordingly, being able to detect biV pulse is generally considered to be important for an automatic diagnostic ECG system, method and algorithm to interpret an ECG waveform accurately. In addition, being able to recognize the existence of biV pacemaker using surface ECG will generally help diagnosis.

In accordance with the present invention, exemplary embodiments of a novel system and method are disclosed and described which are able to detect biV pulses in the regular format of ECG, so exemplary embodiments of the present invention can be used in post-processing or on a central server. Exemplary embodiments of the present invention can be incorporated with certain existing (and anticipated future) non-biV pacemaker pulse detection systems and methods with relatively minimal modification.

Exemplary non-biV pacemaker pulse detector. In accordance with exemplary embodiments of the present invention, a non-biV pacemaker pulse detector is provided. For example, to be able to adopt the invented biV impulse detection system and method with a multi-lead diagnostic ECG system and method, it is possible to minimally modify a non-biV pulse detection system and method to, e.g., increase its pulse width threshold so that it will not fail the detection of a double width pulse, which could be the fusion of a pair of separated ventricular pulses. For example, exemplary embodiments of the non-biV pulse detection system and method will find the onsets of the ventricular pulses and pass the information to the lead-wise biV pulse detector or the vector-based biV pacemaker pulse detector. Also in accordance with certain exemplary embodiments of the present invention, it is possible to, e.g., modify the threshold of the impulse width of the non-biV pulse detector so that it can be used with exemplary embodiments of the present invention.

Exemplary VCG transform. In accordance with exemplary embodiments of the present invention, exemplary VCG transform system and method are provided. For example, exemplary embodiments of this system and method will transform a multi-lead ECG to a 3-dimensional VectorCardioGraph (VCG) which comprises the values in x, y and z directions, respectively. It is possible to use existing VCG transform methods in accordance with exemplary embodiments of the present invention. For example, it is possible to use, e.g., Levkov transform to convert 12-lead ECG to VCG in accordance with exemplary embodiments of the present invention.

Exemplary lead-wise biventricular pacemaker pulse detector. In accordance with exemplary embodiments of the present invention, it is possible that some distant enough biV pulses could be recognized by checking the pulse detection results across all leads. For example, this component looks at the pulse detection result of each single lead to identify the eligible biV paced cases.

Figure 5:
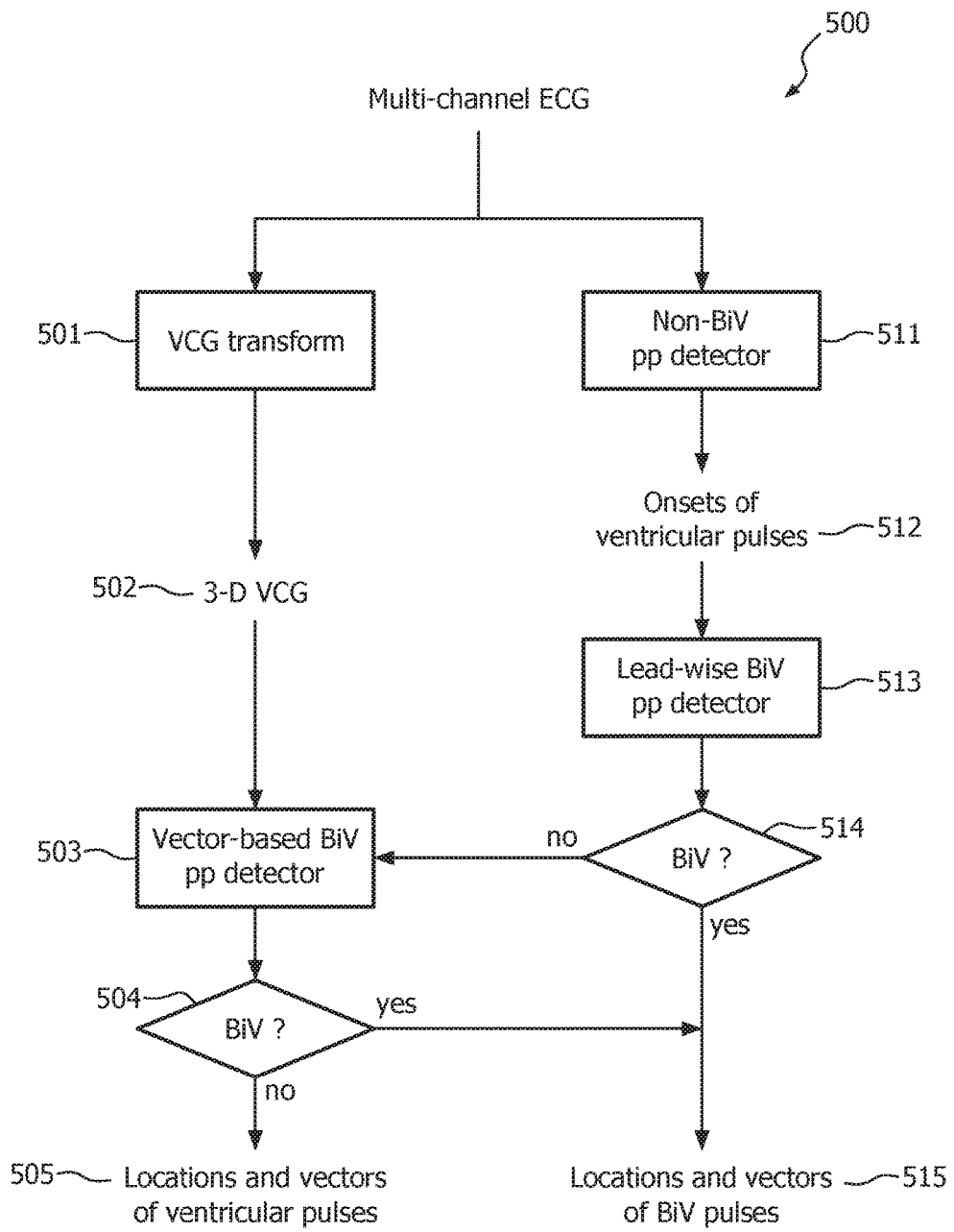
FIG. 5 is a flow chart of an exemplary embodiment of a system and method in accordance with the present disclosure.

An exemplary combination block diagram and flow chart of an exemplary embodiment of a biventricular pace pulse detector 500, detection system 500 and detection method 500 in accordance with the present invention is illustrated in FIG. 5, for example. First, the non-biV pulse detector, detection system and/or detection method 511 processes the ECG signal to find the onsets of ventricular pulses at step 512. For some biV paced cases with distant enough ventricular pulses, both ventricular pulses can be detected. Therefore, the lead-wise biV pulse detector 513 will check whether there are two ventricular pulses in one beat (e.g., two pulses near the onset of QRS) at step 514. If the result is yes, then the beat is a biV paced beat, and the process proceeds to step 515 where no further action is needed. Otherwise, the vector-based biV pulse detector 503 will be used to further check the existence of the second ventricular pulse at step 504. In accordance the present invention, exemplary embodiments of the vector-based biV pulse detector 503 can use 3-D vector features to accomplish this task. Exemplary embodiments of system and method according to the present invention can output the locations and vectors of the detected ventricular pulses as a result.

Figure 6:
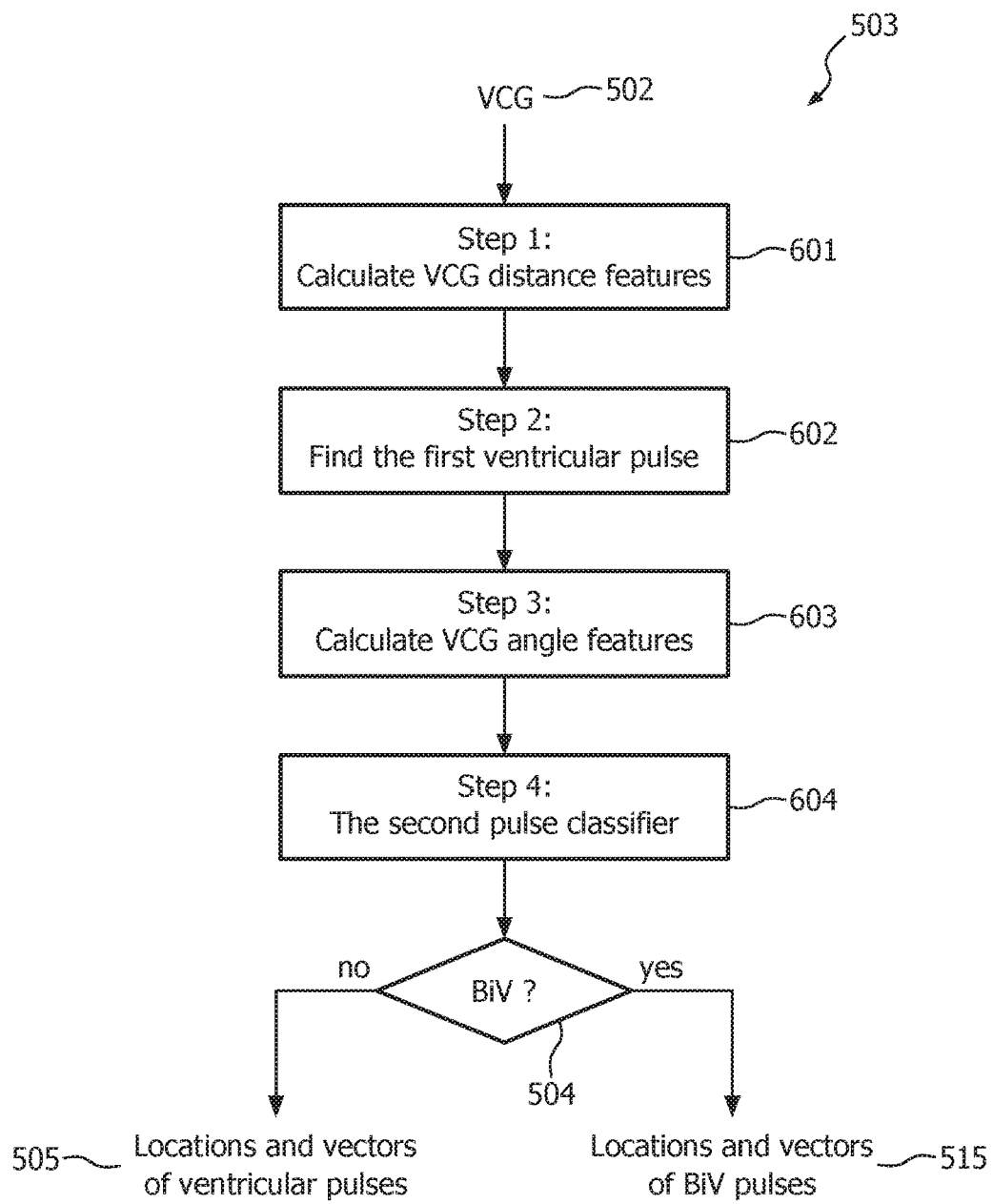
FIG. 6 is a block diagram of an exemplary vector-based biventricular pacemaker pulse detector in accordance with the present disclosure.

Exemplary vector-based biventricular pacemaker pulse detector. FIG. 6 illustrates a block diagram of an exemplary vector-based biventricular pacemaker pulse detector 503 in accordance with exemplary embodiments of the present invention. For example, this detector 503 is able to find whether there is a pulse separable from the first pulse, so it can be considered a second pulse. To be eligible as a pulse, a 3-D vector typically needs to have significant value and change in amplitude. To be separable, two 3-D vectors typically need to have enough distance in time or in angle from one another. Further, the impulse response of the low-pass filter on the first pulse and the recharging wave of the first pulse typically need to be discounted from the selection of a possible biventricular pacemaker pulse.

Figure 7:
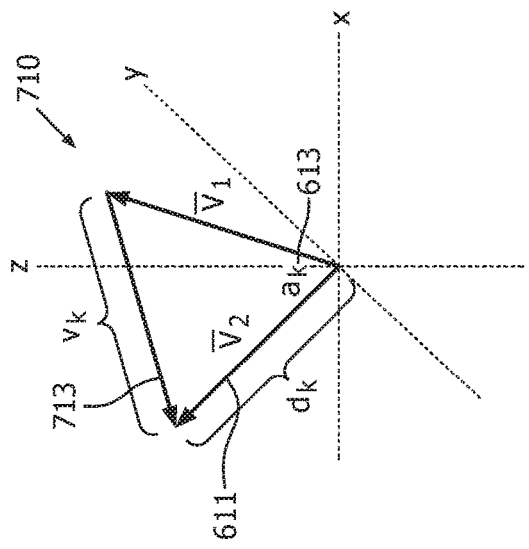
FIG. 7 is an example illustration of defined VCG distance features: spatial distance and spatial velocity, in accordance with the present disclosure.

As illustrated in FIG. 6, for example, in Step 1 601, the VCG signal 502 of a predefined window size starting from the onset of the detected ventricular pulse of a beat is calculated for the VCG distance features: spatial distance and spatial velocity, which can be defined as illustrated in FIG. 7, for example. A major characteristic of a pacemaker pulse is typically a sharp change of amplitude, so minimum threshold values for both spatial distance and spatial velocity can be used for screening pacemaker pulses. Among the VCG vectors with spatial velocity larger than its threshold in the first 10 msec, for example, the vector with maximal spatial distance is selected as the first pulse in Step 2 602. The angle between each vector to the first pulse is calculated in Step 3 603. Further, as illustrated in FIG. 6, in Step 4 604 each vector is checked for a possible 2nd ventricular pulse using the classifier of features: spatial distance, velocity, angle and the temporal distance to the first pulse, for example. The $1^{st}$ v-pulse is the vector with maximum spatial distance (absolute value of amplitude). A vector will be classified to decide whether it is the $2^{nd}$ v-pulse using VCG feature.

FIG. 7 shows how the VCG distance features: spatial distance and spatial velocity, can be defined in accordance with exemplary embodiments of the present invention. A VCG signal 502 is obtained or calculated and expressed as its vector components. For example, spatial distance $d_k$ 611 can be calculated, e.g., in Step 1 601 illustrated in FIG. 6. Spatial velocity $v_k$ 713 can be calculated as shown in representation 703 of FIG. 7. Spatial angle $a_k$ 613 can be calculated in Step 4 603. Graphic 710 provides a graphical representation of the relationship of these vectors.

Figure 8:
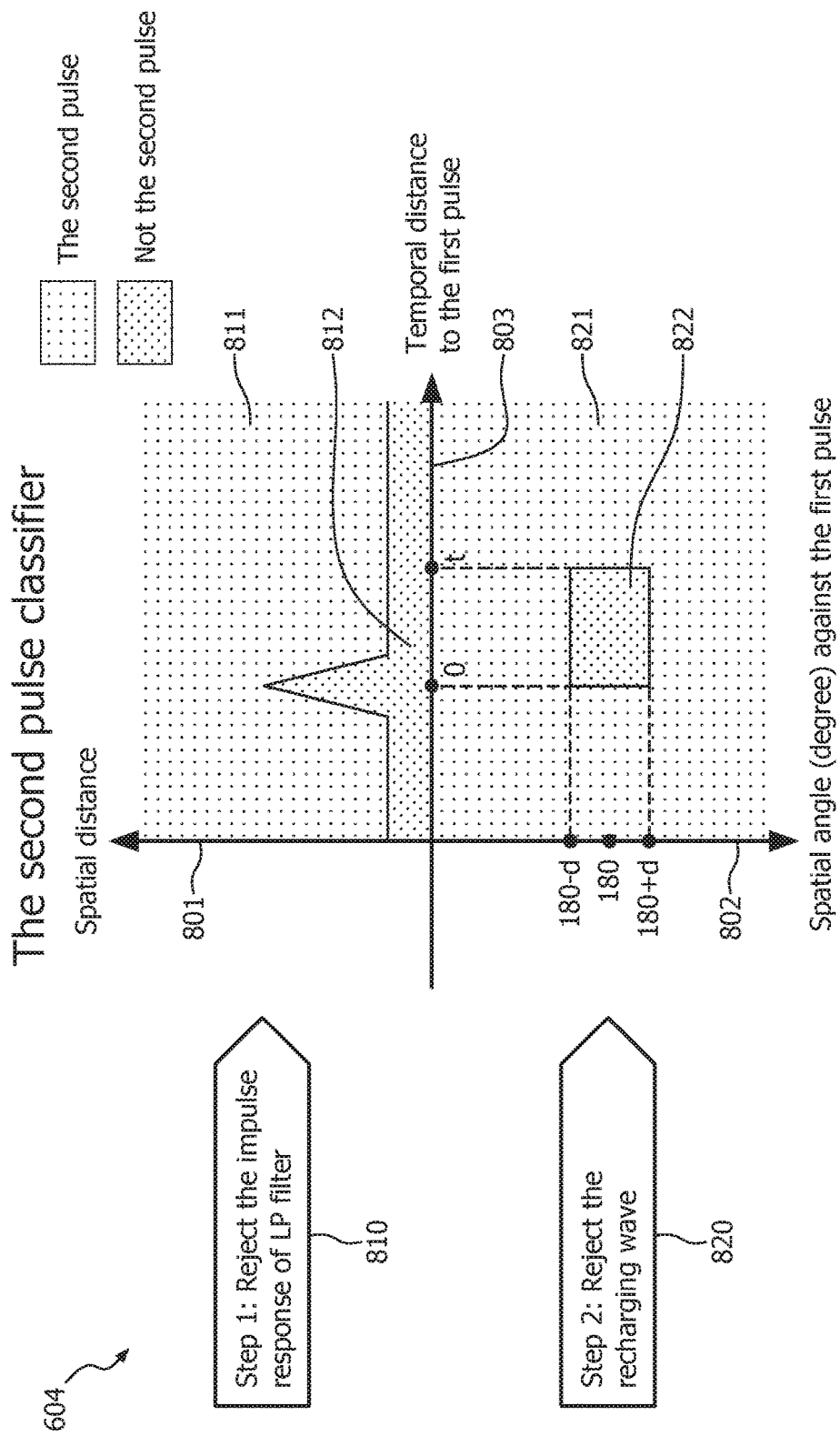
FIG. 8 is an illustration of a classifier in accordance with the present invention.

FIG. 8 illustrates an exemplary embodiment of a pulse classifier 604 in accordance with the present invention. As illustrated in FIG. 8, for example, spatial distance is represented by the top vertical axis 801. Spatial angle (degree) against the $1^{st}$ pulse is represented by the bottom vertical axis 802. Horizontal axis 803 represents the temporal distance to the $1^{st}$ pulse. Exemplary embodiments of classifier 604 can classify vectors using, as shown in Step 1 810, the spatial distance and the temporal distance to the 1st pulse for the exclusion of the low-pass filter impulse response of the $1^{st}$ pulse and vectors without enough amplitude; and, as shown in Step 2 820, the spatial angle against the $1^{st}$ pulse and the temporal distance to the $1^{st}$ pulse for the exclusion of the recharging wave. The main lobe width of the impulse response tends to vary with the low-pass filter. Further, the recharging wave generally will be essentially in the opposite direction of the discharging wave with a deviation and generally follow closely after the discharging pulse. In accordance with exemplary embodiments of the present invention, area 811 of the upper-right quadrant of the graph shown in FIG. 8 illustrates the exclusion of impulse response, and area 821 of the lower-right quadrant of the graph shown in FIG. 8 illustrates the exclusion of the recharging wave. Accordingly, results falling within areas 811 or 821 are indicative of the $2^{nd}$ pulse, while results falling within areas 812 or 822 will not be considered the $2^{nd}$ pulse.

Figure 9:
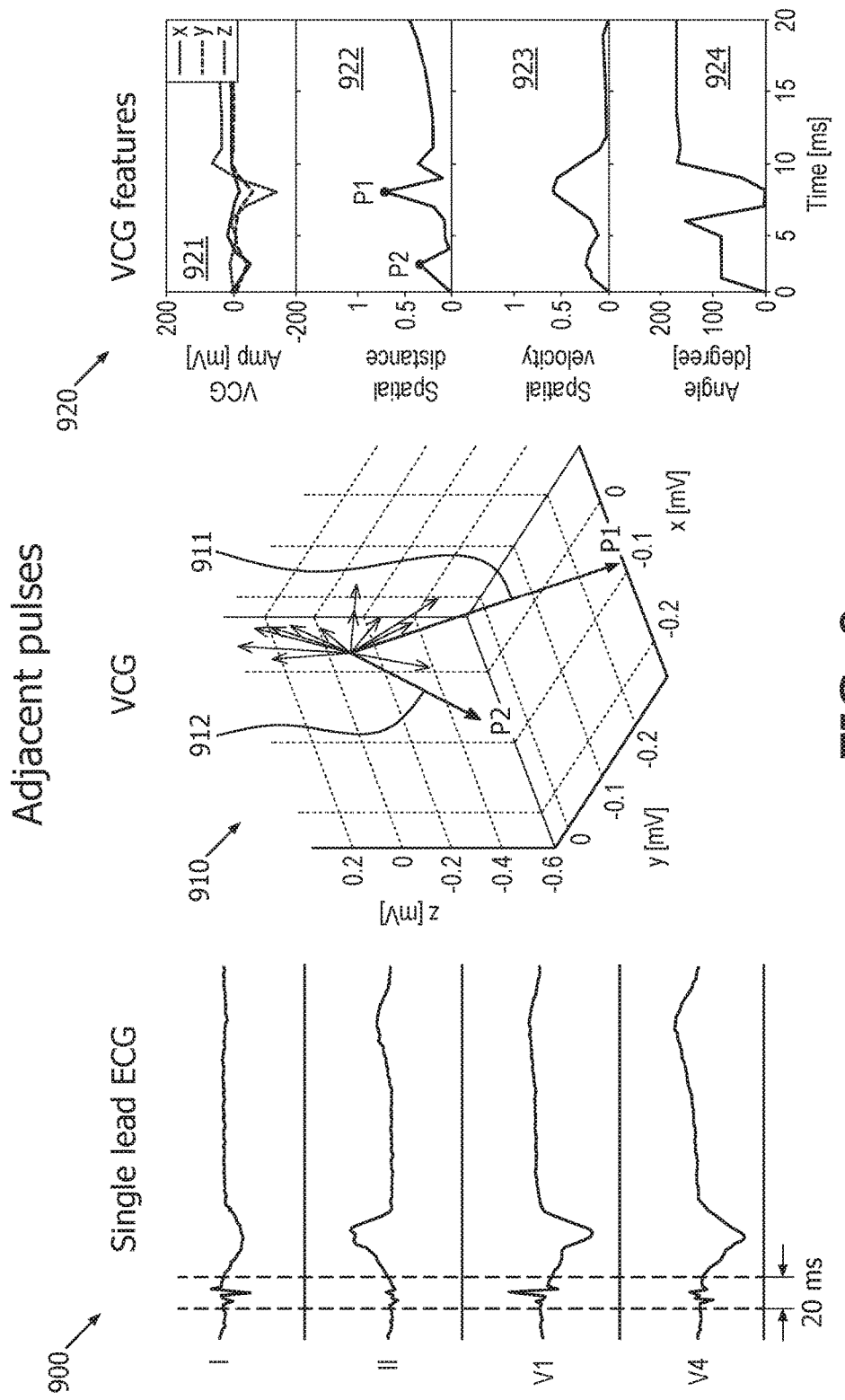
FIG. 9 is an illustration showing an exemplary embodiment of the present disclosure for adjacent ventricular pulses.

FIG. 9 is an example illustration in accordance with exemplary embodiments of the present invention for adjacent pulses. As shown in FIG. 9, graph 900 shows the single beat ECG waveforms of leads I, II, V1 and V4, in which two pulses cannot clearly be seen. However, two pulses P1 911 and P2 912 are clear in the 3-D VCG 910. The 3-D VCG waveforms 921, spatial distance 922, spatial velocity 923 and spatial angle 924 are shown in graphs 920 with the detected two pulses marked within spatial distance graph 922, for example.

Figure 10:
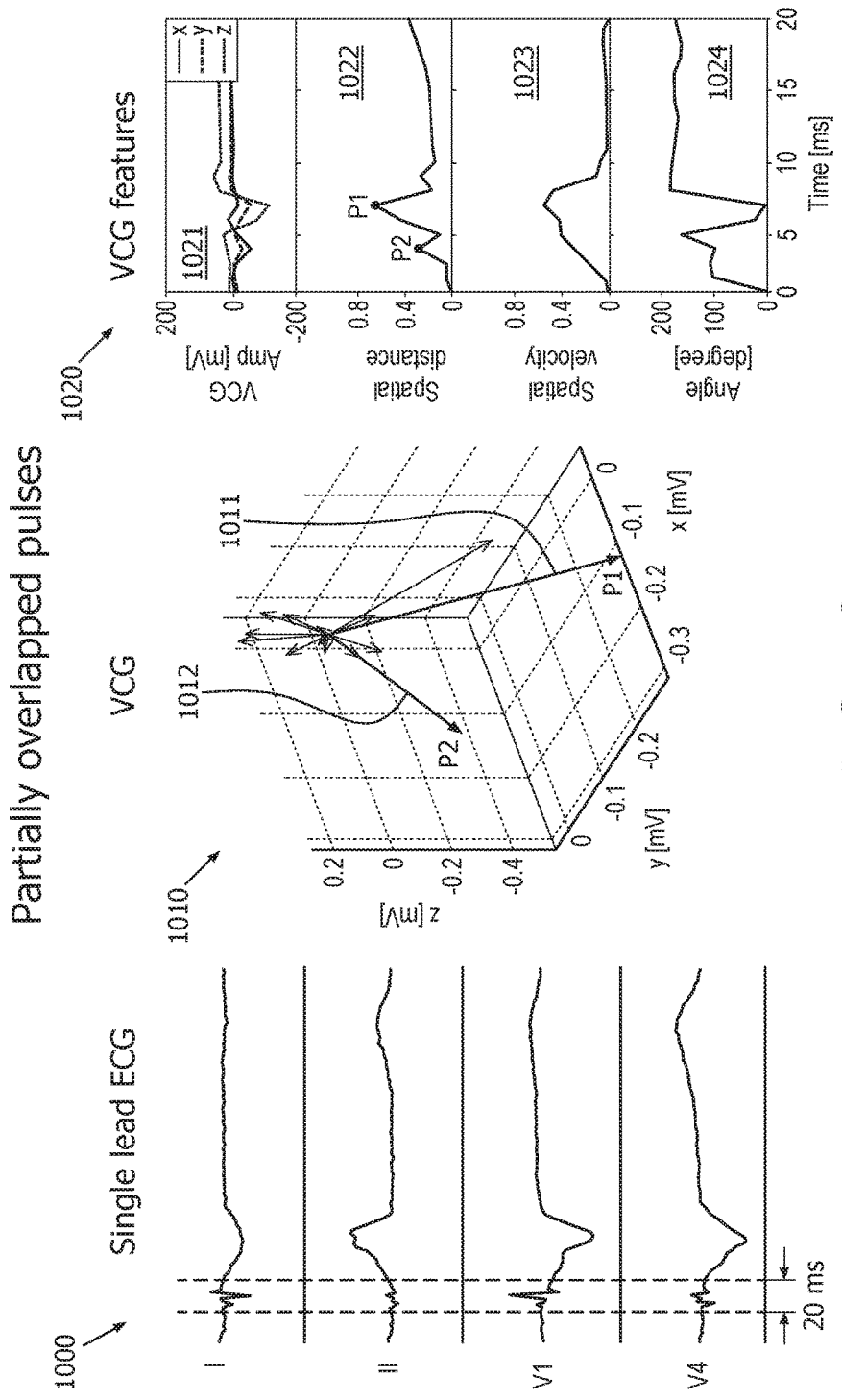
FIG. 10 is an illustration showing an exemplary embodiment of the present disclosure for partially overlapped ventricular pulses.

FIG. 10 is an example illustration in accordance with exemplary embodiments of the present invention for partially overlapped pulses. As shown in FIG. 10, graph 1000 shows the single beat ECG waveforms of leads I, II, V1 and V4, in which two pulses cannot clearly be seen. However, two pulses P1 1011 and P2 1012 are clear in the 3-D VCG 1010. The 3-D VCG waveforms 1021, spatial distance 1022, spatial velocity 1023 and spatial angle 1024 are shown in graphs 1020 with the detected two pulses marked within spatial distance graph 1022, for example.

An exemplary system and method according to the present invention were tested on 500 sps 12-lead ECGs from patients with non-synchronous biV pacing and showed what can be considered to be excellent detection results.

In particular, in accordance with an exemplary embodiment of the present invention, 500 sps continuous 12-lead ECG were collected from 4 patients with biV pacemakers of various manufacturers, while gradually changing RV-to-LV pacing intervals from 70 msec to −70 msec and recording ~30 sec for each interval setting. The two biV pulses could be as close as 2 msec. The ECG waveforms were frequently corrupted with high-frequency noise from nearby devices such as the pacemaker programmer. For system and method training, the continuous ECG recordings were split into a total of 255 cases of 10 sec duration biV paced ECGs, with another 211 cases of 10 sec non-biV paced ECGs randomly selected from an existing pacemaker patient database. When more than 50% of the ventricular paced beats were found with biV pulses in a 10 sec ECG, the ECG was considered biV paced.

Using the above criteria and development dataset, the exemplary system and method showed a detection sensitivity of 94.1% with a detection specificity of 100%. These exemplary results show that non-synchronous biV pacemaker pulses in the surface ECG can be accurately detected using exemplary embodiments of the present invention on existing databases and without the need for hardware modification, even in the presence of significant noise interference.

While this invention has been described with respect to novel and inventive system and method for biventricular pacemaker pulse detection in surface ECG, one having ordinary skill in the art shall appreciate in view of the teaching provided herein that exemplary embodiments of the present invention can be implemented in a wide range of medical devices, including, but not limited to, patient monitors (e.g., ECG monitors), automatic external defibrillators (AEDs) and/or other defibrillators. Indeed, exemplary embodiments of the present invention implemented in these and other types of products are specifically contemplated and considered to be within the scope of the present invention. For example, exemplary embodiments of the present invention can be specifically implemented in/with virtually any multiple-leads diagnostic ECG analysis program running on cardiograph, patient monitor, telemetry monitor or automatic external defibrillator able to detect biventricular pp on regular or low sampling rate hardware (<5000 sps) and/or virtually any multiple-leads diagnostic ECG analysis program using vector to detect biventricular pp. Indeed, as one having ordinary skill in the art shall appreciate in view of the teachings provided herein, exemplary applications of the present invention include, but are certainly not limited, e.g., Multiple-lead diagnostic ECG analysis, cardiograph, patient monitor, telemetry monitor, AED and other monitor and defibrillators.

Further, as one having ordinary skill in the art will appreciate in view of the teachings provided herein, features, elements, components, etc. described in the present disclosure/specification, including the Appendix, and/or depicted in the appended Figures may be implemented in various combinations of hardware and software, and provide functions which may be combined in a single element or multiple elements. For example, the functions of the various features, elements, components, etc. shown/illustrated/depicted in the Figure can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments for novel and inventive system and method for biventricular pacemaker pulse detection in surface ECG, (which embodiments are intended to be illustrative and not limiting), it is noted that modifications and variations can be made by persons skilled in the art in light of the teachings provided herein, including the appended Figure(s) and claims. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A method for locating an existence of a biventricular pace pulse for electrocardiograph (ECG), comprising:
    transforming ECG data to a 3-dimensional VectorCardioGraph (VCG);
    calculating VCG distance features comprising spatial distance and spatial velocity;
    locating a first ventricular pulse;
    calculating VCG angle features including angles between vectors and the first ventricular pulse;
    determining the existence of the biventricular pace pulse by classifying vectors based on spatial distance, spatial velocity, VCG angle features and temporal distances of vectors to the first ventricular pulse, wherein:
        an impulse response of a low-pass filter is rejected from being classified as the biventricular pace pulse based on the spatial distances and the temporal distances of the vectors to the first ventricular pulse;
        a recharging wave is rejected from being classified as the biventricular pace pulse based on the angles between the vectors and the first ventricular pulse and temporal distances of the vectors to the first ventricular pulse; and
        the biventricular pace pulse is determined to exist if an eligible pulse vector exists after performing said rejections.

2. The method of claim 1, wherein the first ventricular pulse is located by determining a vector having a largest spatial distance out of all vectors that have a spatial velocity that exceeds a spatial velocity threshold.

3. The method of claim 1, wherein the ECG data includes two adjacent ventricular pulses per heartbeat.

4. The method of claim 1, wherein the ECG data includes two partially overlapping ventricular pulses per heartbeat.

5. The method of claim 1, further comprising displaying single beat ECG waveforms of the ECG data.

6. A system for locating an existence of a biventricular pace pulse for electrocardiograph (ECG), comprising:
    a non-biventricular pulse detector configured to find onsets of one or more ventricular pulses;
    a lead-wise biventricular pulse detector for determining whether there are two separated ventricular pulses in one heart beat; and
    a vector-based biventricular pulse detector configured to determine the existence of the biventricular pace pulse if the lead-wise biventricular pulse detector does not determine that there are two separated ventricular pulses in one heartbeat,
    wherein the vector-based biventricular pulse detector is configured to:
    calculate VectorCardioGraph (VCG) distance features comprising spatial distance and spatial velocity,
    find a first ventricular pulse,
    calculate VCG angle features including angles between vectors and the first ventricular pulse, and
    determine the existence of the biventricular pace pulse by classifying vectors based on spatial distance, spatial velocity, VCG angle features and temporal distances of vectors to the first ventricular pulse, wherein the vector-based biventricular pulse detector is configured to:
        reject an impulse response of a low-pass filter from being classified as the biventricular pace pulse based on the spatial distances and the temporal distances of the vectors to the first ventricular pulse;
        reject a recharging wave from being classified as the biventricular pace pulse based on the angles between the vectors and the first ventricular pulse and temporal distances of the vectors to the first ventricular pulse; and
        determine that the biventricular pace pulse exists if an eligible pulse vector exists after performing said rejections.

7. The system of claim 6, wherein the vector-based biventricular pulse detector is configured to identify the first ventricular pulse by determining a vector having a largest spatial distance out of all vectors that have a spatial velocity that exceeds a spatial velocity threshold.

8. The system of claim 6, wherein the system has a sampling rate that is less than 5000 samples per second.

9. A vector-based biventricular pace pulse detector, comprising:
    a processor configured to:
    calculate VectorCardioGraph (VCG) distance features comprising spatial distance and spatial velocity,
    find a first ventricular pulse,
    calculate VCG angle features including angles between vectors and the first ventricular pulse, and
    determine an existence of a biventricular pace pulse by classifying vectors based on spatial distance, spatial velocity, VCG angle features and temporal distances of vectors to the first ventricular pulse, wherein the processor is configured to:
        reject an impulse response of a low-pass filter from being classified as the biventricular pace pulse based on the spatial distances and the temporal distances of the vectors to the first ventricular pulse;
        reject a recharging wave from being classified as the biventricular pace pulse based on the angles between the vectors and the first ventricular pulse and temporal distances of the vectors to the first ventricular pulse; and
    determine that the biventricular pace pulse exists if an eligible pulse vector exists after performing said rejections.

10. The detector of claim 1, wherein the processor is configured to identify the first ventricular pulse by determining a vector having a largest spatial distance out of all vectors that have a spatial velocity that exceeds a spatial velocity threshold.

11. The detector of claim 9, further comprising an input configured to receive electrocardiograph (ECG) data.

12. The detector of claim 11, wherein the processor is further configured to transform the ECG data to a 3-dimensional VCG.

13. The detector of claim 9, wherein the detector has a sampling rate that is less than 5000 samples per second.

* * * * *